United States Patent [19]

Yevich et al.

[11] Patent Number: 4,656,173
[45] Date of Patent: Apr. 7, 1987

[54] ANTIPSYCHOTIC BENZISOTHIAZOLE S-OXIDE COMPOUND

[75] Inventors: Joseph P. Yevich, Newburgh; Walter G. Lobeck, Jr., Evansville, both of Ind.

[73] Assignee: Bristol-Myers Company, New York, N.Y.

[21] Appl. No.: 726,449

[22] Filed: Apr. 24, 1985

[51] Int. Cl.$^4$ .................. A61K 31/495; C07D 417/14
[52] U.S. Cl. ..................... 514/253; 514/252; 544/230; 544/360; 544/368
[58] Field of Search .............. 544/230; 514/252, 253

[56] References Cited

U.S. PATENT DOCUMENTS

| | | | |
|---|---|---|---|
| 3,907,801 | 9/1975 | Wu et al. | 544/230 |
| 4,411,901 | 10/1982 | Temple et al. | 544/360 |
| 4,452,799 | 6/1984 | Temple et al. | 544/360 |
| 4,524,206 | 6/1985 | New et al. | 544/230 |

FOREIGN PATENT DOCUMENTS 2114119 8/1983 United Kingdom .

OTHER PUBLICATIONS

Kwan, et al., *International Journal of Pharmaceutics,* 1980, 6, 237–241.

*Primary Examiner*—Donald G. Daus
*Assistant Examiner*—C. Shen
*Attorney, Agent, or Firm*—Robert H. Uloth; Richard P. Ryan

[57] ABSTRACT

8-[4-[4-(1-Oxo-1,2-benzisothiazol-3-yl)-1-piperazinyl]-butyl]-8-azaspiro[4.5]decane-7,9-dione is an antipsychotic agent having reduced side effect liability.

3 Claims, No Drawings

ANTIPSYCHOTIC BENZISOTHIAZOLE S-OXIDE COMPOUND

BACKGROUND OF THE INVENTION

This invention generally pertains to a heterocyclic carbon compound having drug and bio-affecting properties and to its preparation and use. In particular, the invention is concerned with the S-oxide derivative of an antipsychotic benzisothiazole piperazine compound.

In U.S. Pat. No. 4,411,901, issued Oct. 25, 1983, and a related divisional, U.S. Pat. No. 4,452,799, issued June 5, 1984; Temple, et al., disclosed a series of benzisothiazole and benzisoxazole piperazine derivatives having selective antipsychotic activity. A preferred compound of this series, designated BMY 13859, has the structure shown below as 1.

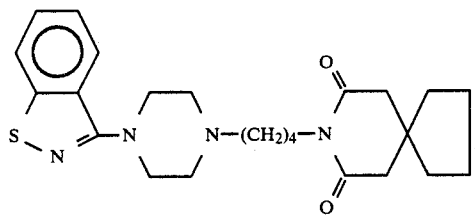

BMY 13859

BMY 13859 is currently being evaluated clinically and appears to be a promising antipsychotic agent.

The compound representing the present invention is the sulfoxide derivative of BMY 13859 and is designated BMY 20366. Of additional interest, metabolic interconversion appears to occur between BMY 13859 and the compound of the instant invention. Metabolic interconversion of sulfides and sulfoxides is known, with the biotransformations of sulindac (2) being reported by Kwan and Heimlich, Internat. J. of Pharmaceutics, 6, (1980) 237-241.

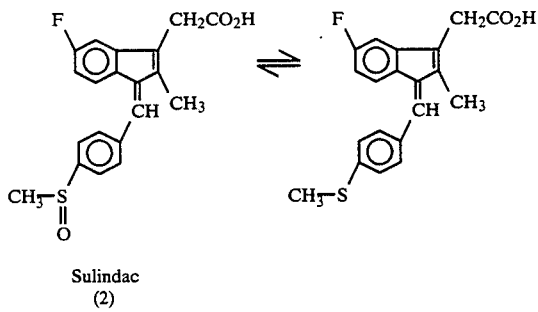

Sulindac
(2)

For sulindac, the pharmacological activity appears to reside only in the sulfide metabolite, which distinguishes sulindac from the instant sulfoxide compound. The instant compound, BMY 20366, appears to be a selective antipsychotic agent possessing a different in vitro binding profile compared with BMY 13859. Expression of pharmacological activity by BMY 20366, the sulfoxide derivative of BMY 13859 would not be obvious from the sulindac art.

SUMMARY AND DETAILED DESCRIPTION OF THE INVENTION

The present invention concerns the compound 8-[4-[4-(1-oxo-1,2-benzisothiazol-3-yl)-1-piperazinyl]butyl]-8-azaspiro[4.5]decane-7,9-dione, whose structure is depicted below as 1 and is also designated BMY 20366.

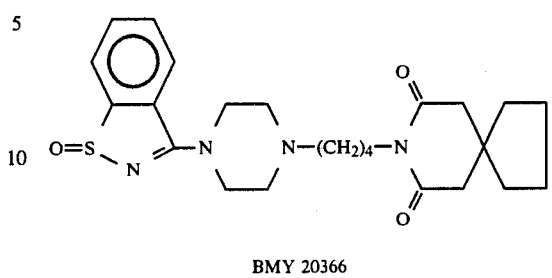

BMY 20366

The invention is also understood to encompass any and all pharmaceutically acceptable acid addition salts of the Formula I compound. By pharmaceutically acceptable acid addition salts is meant those salts in which the anion does not contribute significantly to the toxicity or pharmacological activity of the salt and, as such, they are the pharmacological equivalents of the base of the Formula I compound. They are generally preferred for medical usage; in some instances, they have physical properties which make them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of the base form of the Formula I compound with the selected acid preferably by contacting solutions employing an excess of commonly used inert solvents such as ether, water, benzene, ethanol, ethyl acetate, and acetonitrile. The salt form may also be prepared by any of the other standard methods detailed in the literature available to many practitioners skilled in the art. Examples of useful organic acids are carboxylic acid such as maleic acid, acetic acid. tartaric acid, propionic acid, fumaric acid, isethionic acid, succinic acid, pamoic acid, cyclamic acid, pivalic acid, and the like; useful inorganic acids are hydrohalide acids such as HCl, HBr, HI; sulfuric acids; phosphoric acids; and the like.

The Formula I compound of this invention may be conveniently prepared by oxidation of BMY 13859. While various oxidative preparatory method may be employed, in general, it was found most convenient to effect the oxidation at low temperatures with mixed sulfuric and nitric acids. This synthetic process is depicted below as Scheme 1.

Scheme 1

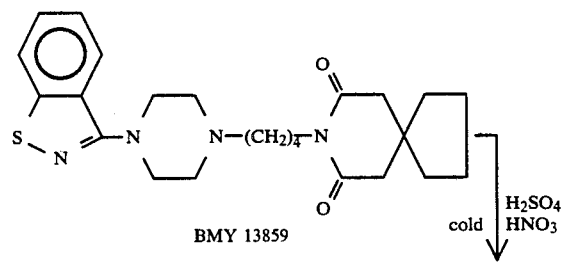

BMY 13859   cold | H₂SO₄ HNO₃

-continued
Scheme 1

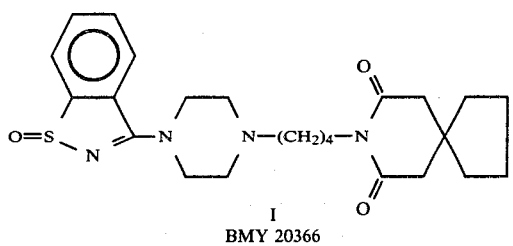

BMY 20366

The compound of the instant invention is a psychotropic agent appearing to have selective antipsychotic activity with a reduced liability for potential side effects. This neuropharmacological profile was established on the basis of the following in vivo tests which are displayed as Table 1.

Table 1

In Vivo Tests Used to Evaluate Formula I Compounds

1. Conditioned Avoidance Response (CAR)—measure of a drug's tranquilizing activity as determined by its attenuation of avoidance response to electrical shock in trained fasted rats. cf: Albert, *Pharmacologist*, 4, 152 (1962); Wu, et al, *J. Med. Chem.*, 12, 876–881 (1969).
2. Inhibition of Apomorphine-Induced (APO) Stereotypy —an assessment of blockade of dopaminergic activity in rats as measured by attenuation of the behavioral syndrome caused by the dopamine agonist, apomorphine. cf: Janssen, et al., *Arzneimittel. Forsch.*, 17, 841 (1966).
3. Catalepsy—drug-induced catalepsy in rats is predictive of potential extrapyramidal symptoms (EPS) in man. cf: Costall, et al, *Psychopharmacologia*, 34, 233–241 (1974); Berkson, *J. Amer. Statist. Assoc.*, 48, 565–599 (1953).
4. Catalepsy Reversal—measure of a drug's ability to reverse neuroleptic-induced catalepsy in the rat.

According to the neuropharmacological profile established by these tests, the instant compound of Formula I has promising antipsychotic potential by virtue of potent activity in both the CAR and APO stereotypy tests. Additionally, the instant compound was found to be be inactive (oral $ED_{50} > 30$ mg/kg) in inducing catalepsy. The results obtained in this battery of in vivo tests for the Formula I compound were similar to the results obtained with BMY 13859.

Differences in neuropharmacological profiles for these two agents may be predicted on the basis of in vitro receptor binding test. Some comparative test results are displayed in Table 2.

TABLE 2

| Receptor Binding Site | Predictive Correlate | $IC_{50}$ (nM) BMY 13859 | Compound I |
|---|---|---|---|
| Dopaminergic ($D_2$) | Antipsychotic efficacy, EPS liability | 10 | >1000 |
| Serotoninergic ($S_2$) | Lack of EPS (?) | 1 | 300 |
| α-adrenergic ($α_1$) | Postural hypotension, palpitations | 50 | 330 |
| Muscarinic | Dry mouth, Constipation | >>1000 | >>1000 |

As can be seen from the binding data in Table 2, compound I would appear to offer an improvement in side effect liability over the agent BMY 13859.

Interestingly, it has been found that when BMY 13859 is administered to either rats or humans, a compound which co-elutes (high pressure liquid chromatography) with compound I is formed. Currently, there is insufficient information available to confirm that compound I is a metabolite of BMY 13859. It is confirmed, however, that authentic BMY 13859 is formed in rats after administration of compound I. It therefore seems likely that a type of chemical interconversion between BMY 13859 and compound I is established in a mammal following administration of either agent. Such interconversions have been previously reported, as for sulindac, supra.

Nonetheless, differing in vivo pharmacological profiles could be displayed by the two agents, BMY 13859 and Compound I, due to differential effects of the pharmacokinetics of distribution, metabolism, and tissue absorption prior to significant chemical interconversion. This interconversion does not appear to be an equilibrium process. The agent that is administered, either BMY 13859 or BMY 20366, is the predominant agent in the blood plasma of rats, being several-fold higher in concentration than the other (interconverted) agent 30 minutes after dosing. In this regard, compound I represents an antipsychotic agent giving an improved neuropharmacological profile compared with BMY 13859.

A selected compound, the dioxide (II) which represents another putative metabolite, was synthesized and tested but has been found to be devoid of antipsychotic activity.

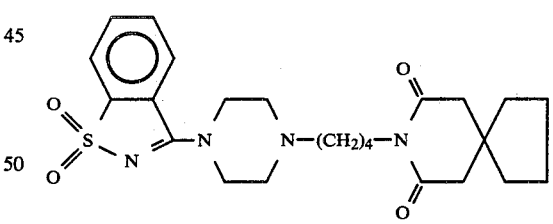

II

In summary, compound I has psychotropic properties particularly suited to its use as an antipsychotic (neuroleptic) agent. Thus, another aspect of the instant invention concerns a process for ameliorating a psychotic state in a mammal in need of such treatment which comprises systemic administration to such mammal of an effective dose of the Formula I compound or a pharmaceutically acceptable acid addition salt thereof.

The administration and dosage regimen for compound I is considered to be done in the same manner as for the reference compound chlorpromazine, cf: AMA Drug Evaluations, 4th Edition, (1980), page 175–176. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably, 0.1 to 2 mg/kg, when administered parenterally; and from about 1 to about 50 mg/kg, preferably 2 to 30 mg/kg, when administered orally. In some instances, a sufficient therapeutic effect can be obtained at lower doses while in others, larger doses will be required. The term "systemic administration" as used herein refers to oral, rectal, and parenteral, i.e., intramuscular, intravenous, and subcutaneous routes. Generally, it will be found that when a compound of the present invention is administered orally, which is the preferred route, a larger quantity of the active agent is required to produce the same effect as a smaller quantity given parenterally. In accordance with good clinical practice, it is preferred to administer the instant compounds at a concentration level that will produce effective antipsychotic (neuroleptic) effects without causing any harmful or untoward side effects.

Therapeutically, compound I would generally be given as a pharmaceutical composition comprised of an effective antipsychotic amount of the Formula I compound when in purified pharmaceutical form or a pharmaceutically acceptable acid addition salt thereof and a pharmaceutically acceptable carrier. Pharmaceutical compositions for effecting such treatment will contain a major or minor amount, e.g. from 95 to 0.5% of the instant compound of the present invention in combination with a pharmaceutical carrier, the carrier comprising one or more solids, semi-solid, or liquid diluent, filler, and formulation adjuvant which are non-toxic, inert and pharmaceutically acceptable. Such pharmaceutical compositions are preferably in dosage unit forms; i.e., physically discrete units containing a pre-determined amount of the drug corresponding to a fraction or multiple of the dose which is calculated to produce the desired therapeutic effect. The dosage units can contain from one to four or more single doses, or, alternatively, one-half to one-quarter or less of a single dose. A single dose preferably contains an amount sufficient to produce the desired therapeutic effect upon administration at one application of one or more dosage units according to the pre-determined dosage regimen, usually a whole, half, third, or quarter of the daily dose administered once, twice, three or four times a day. Other therapeutic agents may also be present. Pharmaceutical compositions which provide from about 1 to 500 mg. of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragacanth, or polyvinyl pyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of compound I with conventional pharmaceutical vehicles are employed for parenteral compositions such as aqueous solutions for intravenous injection or oily suspensions for intramuscular injection. Such compositions having the desired clarity, stability, and adaptability for parenteral use are obtained by dissolving from 0.1% to 10% by weight of the Formula I compound in water or a vehicle consisting of a polyhydric aliphatic alcohol such as glycerine, propylene glycol, and polyethylene glycols or mixtures thereof. The polyethylene glycols consist of a mixture of non-volatile, usually liquid, polyethylene glycols which are soluble in both water and inorganic liquids and which have molecular weights of from about 200 to 1500.

DESCRIPTION OF SPECIFIC EMBODIMENTS

The following example is given for the purpose of illustration only and is not to be construed as limiting the invention in sphere or scope. All temperatures are understood to be in degrees C when not specified. The nuclear magnetic resonance (NMR) spectral characteristics refer to chemical shifts ($\delta$) expressed in parts per million (ppm) vesus tetramethylsilane (TMS) as reference standard. The relative area reported for the various shifts in the proton (PMR) spectral data corresponds to the number of hydrogen atoms of a particular functional type in the molecule. The nature of the shifts as to multiplicity is reported as broad singlet (s), singlet (s), multiple (m), doublet (d), doublet of doublets (dd), triplet (t), or quarter (q). Abbreviations employed are DMSO-$d_6$ perdeuterodimethylsulfoxide, $CDCl_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent.

EXAMPLE 1

8-[4-[4-(1-Oxo-1,2-benzisothiazol-3-yl)-1-piperazinyl]-butyl]-8-azaspiro[4,5]decane-7,9-dione (BMY 20366)

The BMY 13959 (as the hydrochloride salt) may be prepared according to the synthetic methodology given in the Temple, et al., patents cited hereinabove which are hereby incorporated by reference in entirety.

BMY 13859 (as the hydrochloride salt, 12 g, 0.025 mole) was stirred at room temperature in 36 mL of sulfuric acid. After 2 to 3 hours of stirring, the hydrochloride salt had completely dissolved and the resulting solution was chilled (ice and salt bath) to $-2°$ C. A mixture of dilute nitric acid (12 mL HNO$_3$ and 12 mL H$_2$O) was added dropwise. The rate of addition was regulated so that the reaction temperature remained below 5° C. Following completion of the addition, the reaction mixture was stirred for an additional ½ hour. The reaction was worked up by pouring the reaction mixture on ice and then making this acid mixture basic with solid Na$_2$CO$_3$. The basic mixture was extracted (methylene chloride) and the extracts dried (MgSO$_4$), filtered and concentrated in vacuo to 11 g of residue. The residue was dissolved in hot ethanol (60 mL), filtered, and allowed to cool. After several days, the solid which had slowly precipitated was isolated by filtration and dried to give 6.5 g (57% yield) of beige solid, m.p. 149°–151° C.

Anal. Calcd. for $C_{24}H_{32}N_4O_3S$: C, 63.13; H, 7.06; N, 12.29. Found: C, 62.77; H, 7.13; N, 12.36.

NMR (DMSO-$d_6$): 1.49 (12,m); 2.37 (2,m); 2.56 (4,m); 2.65 (4,s); 3.70 (2,t [7.0 Hz]); 3.99 (4,m); 7.75 (2,m); 8.15 (2,m).

IR (KBr): 670, 1070, 1130, 1265, 1360, 1445, 525, 1670, 1720, 2950.

What is claimed is:

1. The compound 8-[4-[4-(1-oxo-1,2-benzisothiazol-3-yl)-1-piperazinyl]butyl]-8-azaspiro[4.5]decane-7,9-dione and its pharmaceutically acceptable acid addition salts.

2. The method for ameliorating a psychotic state in a mammal comprising administration to said mammal of an effective antipsychotic amount of 8-[4-[4-(1-oxo-1,2-benzisothiazol-3-yl)-1-piperazinyl]butyl]-8-azaspiro[4.5]decane-7,9-dione or a pharmaceutically acceptable acid addition salt thereof.

3. A pharmaceutical composition in dosage unit form suitable for systemic administration to a mammalian host comprising a pharmaceutical carrier and from about 1-500 mg of 8-[4-[4-(1-oxo-1,2-benzisothiazol-3-yl)-1-piperazinyl]butyl]-8-azaspiro[4.5]decane-7,9-dione or a pharmaceutically acceptable acid addition salt thereof.

* * * * *